US007361684B2

(12) United States Patent
Krieger et al.

(10) Patent No.: US 7,361,684 B2
(45) Date of Patent: Apr. 22, 2008

(54) SCREENING OF COMPOUNDS FOR TREATMENT OF ATHEROSCLEROSIS AND HEART ATTACK

(75) Inventors: Monty Krieger, Needham, MA (US); Anne Braun, Strasbourg (FR); Helena E. Miettinen, Helsinki (FI)

(73) Assignee: Massachusetts Institute of Technology, Cambridge, MA (US)

( * ) Notice: Subject to any disclaimer, the term of this patent is extended or adjusted under 35 U.S.C. 154(b) by 905 days.

(21) Appl. No.: 10/147,651

(22) Filed: May 16, 2002

(65) Prior Publication Data
US 2003/0046718 A1    Mar. 6, 2003

Related U.S. Application Data

(63) Continuation-in-part of application No. 09/606,324, filed on Jun. 28, 2000, now Pat. No. 6,437,215.

(60) Provisional application No. 60/164,679, filed on Nov. 10, 1999, provisional application No. 60/141,361, filed on Jun. 28, 1999.

(51) Int. Cl.
*A01N 43/16* (2006.01)
*A61K 31/355* (2006.01)

(52) U.S. Cl. .................. 514/458; 514/469; 514/474; 514/712; 514/824

(58) Field of Classification Search ................ 800/3, 800/14, 13, 18; 514/458, 469, 474, 712, 514/824
See application file for complete search history.

(56) References Cited

U.S. PATENT DOCUMENTS

| | | | |
|---|---|---|---|
| 3,625,214 A | | 12/1971 | Higuchi et al. |
| 4,789,734 A | | 12/1988 | Pierschbacher |
| 4,906,474 A | | 3/1990 | Langer et al. |
| 4,925,673 A | | 5/1990 | Steiner et al. |
| 5,494,936 A | * | 2/1996 | Sanchez et al. ............. 514/712 |

FOREIGN PATENT DOCUMENTS

WO    WO 96/00288 A2    1/1996

OTHER PUBLICATIONS

Prelle, K. et al. Establishment of Pluripotent Cell Lines from Vertebrate Species—Present Status and Future Prospects. Cells Tissues Organs. 1999, vol. 165, pp. 220-236.*
Moreadith, R. W. Gene Targeting in Embryonic Stem Cells: the New Physiology and Metabolism. J. Molecular Med. 1997, vol. 75, pp. 208-216.*
Azen, et al. Effect of Supplementary Antioxidant Vitamin Intake on Carotid Arterial Wall Intima-Media Thickness in a Controlled Clinical Trial of Cholesterol Lowering. Circulation. 1996, vol. 94, pp. 2369-2372.*
Noguchi et al. Inhibition of Oxidation of Low-Density Lipoprotein by a Novel Oxidant, BO-653, Prepared by Theoretical Design. Arch. Biochem. Biohys. 1997, vol. 347, pp. 141-147.*
Baldassarre et al. Clinical Evaluation of probucol in Hypercholesterolemia: Individual Lipoprotein Responses and Inhibitory Effect on Carotid Atherosclerosis Progression. J. Cardiovascular Pharmacology. 1997, vol. 30, 784-789.*
BellaOnline, http://www.bellaonline.com/articles/art32665.asp, printed out Sep. 5, 2006.*
Miettinen et al., "Multifactorial primary prevention of cardiovascular diseases in middle-aged men. Risk factor changes, incidence, and mortality," Journal of the American Medical Associateion, vol. 254, No. 15, 1985 (abstract only).*
Miettinen et al. Long-Term Use of Probucol in the Multifactorial Primary Prevention of Vascular Disease. American J. Cardiology. 1986, vol. 57, pp. 49H-54H.*
Mosca et al. Antioxidant Nutrient Supplementation Reduces the Suceptibility of Low Density Lipoprotein to Oxidation in Patients with Coronary Artery Disease. J. American College Cardiology. 1997, vol. 30, pp. 392-399.*
Kessopoulou et al. A Double-Blind Randomized Placebo Cross-Over Controlled Trial Using the Antioxidant Vitamin E to Treat Reactive Oxygen Species Associated with Male Infertility. Fertility Sterility. 1995, vol. 64, pp. 825-831.*
Abumrad, et al., "Cloning of a rat adipocyte membrane protein implicated in binding or transport of long-chain fatty acids that is induced during preadipocyte differentiation," *J. Biol. Chem.* 268:17665-17668 (1993).
Acton, et al., "Expression cloning of SR-BI, a CD36-related class B scavenger receptor," *J. Biol. Chem.* 269:21003-21009 (1994).
Acton, et al., "Identification of Scavenger receptors SR-BI as a high density lipoprotein receptor," *Science* 271:518-520 (1996).

(Continued)

Primary Examiner—Deborah Crouch
(74) Attorney, Agent, or Firm—Pabst Patent Group LLP

(57) ABSTRACT

Transgenic animals that do not express functional SR-BI and ApoE develop severe atherosclerosis, by age four weeks in transgenic mice. Moreover, these animals exhibit progressive heart dysfunction by as early as age four weeks, and die by age nine weeks. This animal model has now been demonstrated to be useful as a screen for compounds which alleviate the symptoms of atherosclerosis and heart disease. Animals (Apo E−/− SR-BI+/−) were fed PROBUCOL beginning at the time of mating. Offspring are weaned at three weeks and fed PROBUCOL. In contrast to animals (Apo E−/− SR-BI−/−) not fed PROBUCOL, 50% of whom are dead at six weeks, all animals (Apo E−/− SR-BI−/−) on PROBUCOL have a normal phenotype (MRI of heart function, ECG, echocardiogram, histology) at six weeks. At seven to eight months, there is evidence of atherosclerosis and some myocardial infarction. This demonstrates that the compound has a preventative action. Animals who are taken off of the PROBUCOL all die within ten to twelve weeks. In another study, the majority of animals whose parents were not fed PROBUCOL, but who received the PROBUCOL beginning at about five weeks of age, survived for a few months, demonstrating that the compound also has a therapeutic benefit.

10 Claims, No Drawings

OTHER PUBLICATIONS

Acton, et al., "The collagenous domains of macrophages scavenger receptors and complement component C1q mediate their similar, but not identical, binding specificities for polyanionic ligands," *J. Biol. Chem.* 268:3530-3537 (1993).

Andersen & Dietschy, "Kinetic parameters of the lipoprotein transport systems in the adrenal gland of the rat determined in vivo," *J. Biol. Chem.* 256:7362 (1981).

Arai, et al., "Decreased atherosclerosis in heterozygous low density lipoprotein receptor-deficient mice expressing the scavenger receptor BI transgene," *J. Biol. Chem.* 274:2366-2371 (1999).

Arai, et al., "Multiple receptors for modified low density lipoproteins in mouse peritoneal macrophages: different uptake mechanisms for acetylated and oxidized low density lipoproteins," *Biochem. Biophys. Res. Commun.* 159:1375-1382 (1989).

Asch, et al., "Isolation of the thrombospondin membranes receptors," *J. Clin. Invest.* 79:1054-1061 (1987).

Azhar, et al., "Simultaneous induction of an HDL receptor protein (SR-BI) and the selective uptake of HDL-sholesteryl esters in a physiologically relevant steroidogenic cell model," *J. Lipid Res.* 39:1616-1628 (1998).

Babitt, et al., "Murine SR-BI, a high density lipoprotein receptor that mediates selective lipid uptake, is N-glycosylated and fatty acylated and colocalizes with plasma membrane caveolae," *J. Biol. Chem.* 272:13242-13249 (1997).

Bickel, et al., "Rabbit aortic smooth muscle cells express inducible macrophages scavenger receptor messengers RNA that is absent from endothelial cells," *J. Clin. Invest.* 90:1450-1457 (1992).

Bolard, "How do the polyene macrolide antibiotics affect the cellular membrane properties?" *Biochim. Biophys. Acta* 864:257-304 (1986).

Bourassa, et al., "Improved method for tissue preservation in murine atherosclerosis lesion tissue," *J. Histotechnology* 21:33-38 (1998).

Brown & Goldstein, "Lipoprotein metabolism in the macrophage: Implications for cholesterol deposition in atherosclerosis," *Annu. Rev. Biochem.* 52:223-261 (1983).

Calvo & Vega, "Identification, primary structure, and distribution of CLA-1, a novel member of the CD36/LIMPII gene family," *J. Biol. Chem.* 268:18929-18935 (1993).

Calvo, et al., "CLA-1 is an 85-kD plasma membrane glycoprotein that acts as a high-affinity receptor for both native (HDL, LDL, and VLDL) and modified (OxLDL and acLDL) lipoproteins," *Arterioscler. Vasc. Biol.* 17:2341-2349 (1997).

Cao, et al., "Structure and localization of the human gene encoding SR-BI/CLA-1," *J. Biol. Chem.* 272:33068-33076 (1997).

Doi, et al., "Charged collagen structure mediates the recognition of negatively charged macromolecules by macrophages scavengers receptors," *J. Biol. Chem.* 268:2126-2133 (1993).

Elvin, et al., "Mouse models of ovarian failure," *Reviews of Reproduction* 3:183-195 (1998).

Endemann, et al., "CD36 is a receptor for oxidized low density lipoprotein," *J. Biol. Chem.* 268:11811-11816 (1993).

Fielding, et al., "Molecular physiology of reverse cholesterol transport," *J. Lipid. Res.* 36:211-228 (1995).

Fielding, et al., "Two-dimensional nondenaturing electrophoresis of lipoproteins: applications to high-density lipoprotein specification," *Methods Enzymol.* 263:251-259 (1996).

Fluiter, et al., "In vivo regulation of scavenger receptor BI and the selective uptake of high density lipoprotein cholesterol esters in rat liver parenchymal and kupffer cells," *J. Biol. Chem.* 273:8434-8438 (1998).

Fraser, et al., "Divalent cation-independent macrophages adhesion inhibited by monoclonal antibody to murine scavenger receptor," *Nature* 364:343-346 (1993).

Freeman, et al., "Expression of type I and type II bovine scavenger receptors in Chinese hamster ovary cells: Lipid droplet accumulation and nonreciprocal cross competition by acetylated and oxidized low density lipoprotein," *Proc. Natl. Acad. Sci. U.S.A.* 88:4931-4935 (1991).

Glass, et al., "Dissociation of tissue uptake of cholesterol ester from that of apoprotein A-I of rat plasma high density lipoprotein: selective delivery of cholesterol ester to liver, adrenal, and gonad," *Proc. Natl. Acad. Sci. USA* 80:5435-5439 (1983).

Glass, et al., "Uptake of high-density lipoprotein-associated apoprotein A-I and cholesterol esters by 16 tissues of the rat in vivo and by adrenal cells and hepatocytes in vitro," *J. Biol. Chem.* 260:744-750 (1985).

Goldstein, et al., "Binding site on macrophages that mediates uptake and degradation of acetylated low density lipoprotein, producing massive cholesterol depositions," *Proc. Natl. Acad. Sci. U.S.A.* 76:333-337 (1979).

Goldstein, et al., in the Metabolic and Molecular Bases of Inherited Disease, Scriver, et al., eds., (McGraw-Hill, NY 1995).

Gordon, et al., "High-density lipoprotein- the clinical implications of regent studies," *N. Engl. J. Med.* 321:1311-1316 (1989).

Greenwalt, et al., "Membrane glycoprotein CD36: A review of its roles in adherence, signal transduction, and transfusion medicine," *Blood* 80:1105-1115 (1992).

Gregoriadis, "Liposomes" in *Drug Carriers in Biology and Medicine* Chapter 14 pp. 287-341 (Academic Press, 1979).

Gu, et al., *J. Biol. Chem.* 273:26338-26348 (1998).

Gwynne, et al., "The role of lipoproteins in steroidogenesis and cholesterol metabolism in steroidogenic glands," *Endocr. Rev.* 3:299-329 (1982).

Haberland, et al., "Two distinct receptors account for recognition of maleyl-albumin in human monocytes during differentiation in vitro," *J. Clin. Inves.* 77:681-689 (1986).

Hatzapoulos, et al., "Temporal and spatial pattern of expression of the HDL receptor SR-BI during murine embryogenesis," *J. Lipid Res.* 39:495-508 (1998).

Hauser, et al., "Identification of a receptor mediating absorption of dietary cholesterol in the intestine," *Biochemistry* 37:17843-17850 (1998).

Herz, et al., "Surface location and high affinity for calcium of a 500-kd liver membrane protein closely related to the LDL-receptor suggest a physiological role as lipoprotein receptor," *EMBO J.* 7:4119-4127 (1988).

Hogan, et al., *Manipulating the mouse embryo*, Cold Spring Harbor Laboratory, Cold Spring Harbor, NY (1986).

Horiuchi, et al., "Scavenger function of sinusoidal liver cells," *J. Biol. Chem.* 259:53-56 (1985).

Huang, et al., "Membrane glycoprotein IV (CD36) is physically associated with the Fyn, Lyn, and Yes protein-tyrosine kinases in human platelets," *Proc. Natl. Acad. Sci. USA* 88:7844-7848 (1991).

Ishida, et al., "Interconversion of prebeta-migrating lipoproteins containing apolipoprotein A-1 and HDL," *J. Lipid Res.* 31:227-236 (1990).

Ji, et al., "Scavenger receptor B1 promotes high density lipoprotein-mediated cellular cholesterol efflux," *J. Biol. Chem.* 272:20982-20985 (1997).

Johnson, et al., "Cholesterol transport between cells and high-density lipoproteins," *Biochim. Biophys. Acta.* 1085:273-298 (1991).

Joyner, et al., "Production of a mutation in mouse *En-2* gene by homologous recombination in embryonic stem cells," *Nature* 338:153-156 (1989).

Kodama, et al., "Type I macrophages scavenger receptor contains α-helix and collagen-like coiled coils," *Nature* 343:531-535 (1990).

Kozarsky, et al., "Overexpression of the HDL receptor SR-BI alters plasma HDL and bile cholesterol levels," *Nature* 387:414-417 (1997).

Krieger & Herz, "Structures and functions of multiligand lipoprotein receptors: Macrophage scavenger receptors and LDL receptor-related protein(LRP)," *Annu. Rev. Biochem.* 63:601-637 (1994).

Krieger, "Charting the fate of the "good cholesterol"; Identification and characterization of the high-density lipoprotein reception SR-BI," *Ann. Rev. Biochem.* 68:523-558 (1999).

Krieger, "Molecular flypaper and atherosclerosis: structure of the macrophage scavenger receptor," *Trends Biochem. Sci.* 17:141-146 (1992).

Landschulz, et al., "Regulation of scavenger receptor, class B, type 1, a high lipoprotein receptor, in liver and steroidogenic tissues of the rat," *J. Clin. Invest.* 98:984-995 (1996).

Li, et al., *Endocrinology* 139:3043-3049 (1998).
Liu, et al., "Ribonucleic acid expression of the CLA-1 gene, a human homolog to mouse high density lipoprotein receptor SR-BI, in human adrenal tumors and cultured adrenal cells," *J. Clin. Endocrinol. Metab.* 82:2522-2527 (1997).
Meiner, et al., "Disruption of the acyl-CoA:cholesterol acyltransferase gene in mice: Evidence suggesting multiple cholesterol esterification enzymes in mammals," *Proc. Natl. Acad. Sci. USA* 93:14041-14046 (1996).
Mizutani, et al., "Cloning, characterization and cellular distribution of rat scavenger receptor class B type 1 (SRBI) in the ovary," *Biochem. Biophys. Res. Commun.* 234:499-505 (1997).
Moestrup, et al., "Distribution of the $\alpha_2$ -macroglobulin receptor/low density lipoprotein receptor-related protein in human tissues" *Cell Tissue Res.* 269:375-382 (1992).
Moreadith, et al., "Gene targeting in embryonic stem cells: the new physiology and metabolism," *J. Mol. Med.* 75(3): 208-216 (1997).
Murao, et al., "Characterization of CLA-1, a human homlologue of rodent scavenger receptor BI, as a high density lipoprotein and apoptotic thymocytes," *J. Biol. Chem.* 272:17551-17557 (1997).
Nagelkerke, et al., "In vivo and in vivo uptake and degradation of acetylated low density lipoprotein by rat liver endothelial, Kupffer, and parenchymal cells," *J. Biol. Chem.* 258:12221-12227 (1983).
Naito, et al., "Tissue distribution, intracellular localization, and in vitro expression of bovine macrophages scavenger receptors," *Am. J. Pathol.* 139:1411-1423 (1991).
Nelson, et al., "A longitudinal study of estrous cyclicity in aging C57BL/6J Mice," *Biol. Reprod.* 27:327-339 (1982).
Ng, et al., "Disruption of the urine lecithin:cholesterol acyltransferase gene causes impairment of adrenal lipid delivery and up-regulation of scavenger receptor class B type I," *J. Biol. Chem.* 272:15777-15781 (1997).
Ockenhouse, et al., "Activation of monocytes and platelets by monoclonal or malarial-infected erythrocytes binding to the CD36 surface receptor in vitro," *J. Clin. Invest.* 84:468-475 (1989).
Oquendo, et al., "CD36 directly mediates cytoadherance of plasmodium falciparum parasitized erythrocytes," *Cell* 58:95-101 (1989).
Oram, et al., "Apolipoprotein-mediated removal of cellular choelsterol and phosholipids," *J. Lipid Res.* 37:2473-2491 (1996).
Ottnad, et al., "Differentiation of binding sites on reconstituted hepatic scavenger receptors using oxidized low-density lipoprotein," *Biochem J.* 281:745-751 (1992).
Paigen, et al., "Quantitative assessment of atherosclerotic lesions in mice," *Atherosclerosis* 68:231-240 (1987).
Pieters, et al., "In vitro and in vivo evidence for the role of HDL in reverse cholesterol transport," *Biochim. Biophys. Acta* 1225:125-134 (1994).
Plump, et al., "ApoA-1 knockout in mice: characterization of HDL metabolism in homolzygotes and identification of a post-RNA mechanism of apoA-1 up-regulation in heterozygotes," *J. Lipid Res.* 38:1033-1047 (1997).
Plump, et al., "Apolipoprotein A-1 is required for cholesteryl ester accumulation in steroidogenic cells and for normal adrenal steroid production," *J. Clin. Invest.* 97:2660-2671 (1996).
Plump, et al., "Severe hypercholersterolemia and atherosclerosis in apolipoprotein E-deficient mice created by homologous recombination in ES cells," *Cell* 71:343-353 (1992).
Potter, et al., "Enhancer-dependent expression of human k immunoglobulin genes introduced into mouse pre-B lymphocytes by electroporation," *Proc. Natl. Acad. Sci. USA* 81:7161 (1984).
Prelle, et al., "Establishment of pluripotent cell lines from vertebrate species—present status and future prospects," *Cells Tissues Organs* 165: 220-236 (1999).
Puglielli, et al., Modulation of intrahepatic cholesterol trafficking: evidence by in vivo antisense treatment for the involvement of sterol carrier protein *Biochem. J.* 317:681-687 (1996).
Rajapaksha, et al., "Sequence of the bovine HDL-receptor (SR-BI) cDNA and changes in receptor mRNA expression during granulosa cell luteinization in vivo and in vitro," *Mol. Cell. Endocrinol.* 134:59-67 (1997).

Reaven, et al., "Expression and microvillar localization of scavenger receptor, class B, type I, a high density lipoprotein receptor) in luteinized and hormone-desensitized rat ovarian models," *Endocrinology* 139:2847-2856 (1998).
Rigotti, et al., "A targeted mutation in the murine gene encoding the high density lipoprotein (HDL) receptor scavenger class B type I reveals its key role in HDL metabolism," *Proc. Natl. Acad. Sci. USA.* 94:12610-12615 (1997).
Rigotti, et al., "Scavenger receptor BI— a cell surface receptor for high density lipoprotein," *Curr. Opin. Lipidol.* 8:181-188 (1997).
Rigotti, et al., "The class B scavenger receptors SR-BI and CD36 are receptors for anionic phospholipids," *J. Biol. Chem.* 270:16221-16224 (1995).
Rigotti, et al., "Regulation by adrenocortotropic hormone of the in vitro expression of scavenger receptor class B Type I (SR-BI), a high density lipoprotein receptor, in steroidogenic cells of the murine adrenal gland," *J. Biol. Chem.* 271:33545-33549 (1996).
Rohrer, et al., "Coiled-coil fibrous domains mediate ligand binding by macrophage scavenger receptor type II," *Nature* 343:570-572 (1990).
Savill, et al., "Macrophage vitronectin receptor, CD36, and thrombospondin cooperate in recognition of neutrophils undergoing programmed cell death," *Chest* 99(3)(suppl):6S-7S (1991).
Schnitzer, et al., "Preferential interaction of albumin-binding proteins, gp30 and gp18, with conformationally modified albumins," *J. Biol. Chem.* 267:24544-24553 (1992).
Sehayek, et al., "Bilary cholesterol excretion: a novel mechanism that regulates dietary cholesterol absorption," *Proc. Natl. Acad. Sci. USA.* 95:10194-10199 (1998).
Southern & Berg, "Transformation of mammalian cells to antibiotic resistance with a bacterial gene under control of the SV40 early region promoter," *J. Mol. Appl. Gen.* 1:327-341 (1982).
Sparrow, et al., "A macrophage receptor that recognizes oxidized low density lipoprotein but not acetylated low density lipoprotein," *J. Biol. Chem* 264:2599-2604 (1989).
Stangl, et al., "Scavenger receptor, class B, type I-dependent stimulation of cholesterol esterification by high density lipoproteins, low density lipoproteins, and nonlipoprotein cholesterol," *J. Biol. Chem.* 273:31002-31008 (1998).
Stanton, et al., "A macrophage Fc receptor for IgG is also a receptor for oxidized low density lipoprotein," *J. Biol. Chem.* 267:22446-22451 (1992).
Steinberg, et al., "Beyond cholesterol. Modification of low-density lipoprotein that increase its atherogenicity," *N. Engl. J. Med.* 320:915-924 (1989).
Suzuki, et al., "A role for macrophage scavenger receptors in atherosclerosis and susceptibility to infection," *Nature* 386:292-296 (1997).
Tall, "Plasma cholesteryl ester transfer protein," *Lipid Res.* 34:1225-1274 (1993).
Tandon, et al., "Identification of glycoprotein IV (CD36) as a primary receptor for platelet-collagen adhesion," *J. Biol. Chem.* 264:7576-7583 (1989).
Temel, et al., "Scavenger receptor class B, type I (SR-BI) is the major route for the delivery of high density lipoprotein cholesterol to the steroidogenic pathway in cultured mouse adrenocortical cells," *Proc. Natl. Acad. Sci. USA*, 94:13600-13605 (1997).
*Teratocarcinomas and embryonic stem cells, a practical approach*, ed. E.J. Robertson, (IRL Press 1987).
Towbin, et al., "Electrophoretic transfer of proteins from polyacrylamide gels to nitrocellulose sheets: procedure and some applications," *Proc. Natl. Acad. Sci. USA* 76:4350-4354 (1979).
Ueda, et al., "Lower plasma levels and accelerated clearance of high density lipoprotein (HDL) and non-HDL cholesterol in scavenger receptor class B type I transgenic mice," *J. Biol. Chem.* 274:7165-7171 (1999).
Varban, et al., "Targeted mutation reveals a central role for SR-BI in hepatic selective uptake of high density lipoprotein cholesterol," *Proc. Natl. Acad. Sci. USA*, 95:4619-4624 (1998).
Via, et al., "Identification and density dependent regulation of the AC-LDL receptor in normal and transformed bovine aortic endothelial cells," *The Faseb J.* 6:A371 (1992).

Wang, et al., "Liver-specific overexpression of scavenger receptor BI decreases levels of very low density lipoprotein ApoB, low density lipoprotein ApoB, and high density lipoprotein in transgenic mice," *J. Biol. Chem.* 273:32920-32926 (1998).

Wang, et al., "Scavenger receptor BI (SR-BI) is up-regulated in adrenal gland in apolipoprotein A-I and hepatic lipase knock-out mice as a response to depletion of cholesterol stores," *J. Biol. Chem.* 271:21001-21004 (1996).

Wyne, et al., "Transport of maternal LDL and HDL to the fetal membranes and placenta of the golden syrian hamster is mediated by receptor-independent processes," *J. Lipid. Res.* 39:518-530 (1998).

Xu, et al., "Apolipoproteins of HDL can directly mediate binding to the scavenger receptor SR-BI, an HDL receptor that mediates lipid uptake," *J. Lipid Res.* 38:1289-1298 (1997).

Zhang, et al., "Diet-induced atherosclerosis in mice heterozygous and homozygous for apolipoprotein E gene disruption," *J. Clin. Invest.* 94:937-945 (1994).

Zhang, et al., "Spontaneous hypercholesterolemia and arterial lesions in mice lacking apolipoprotein E," *Science* 25:468-471 (1992).

Zimmer & Gruss, "Production of chimaeric mice containing embyonic stem (ES) cells carrying a homeobox Hox 1.1 allele mutated by homologous recombination," *Nature* 338:150-153 (1989).

* cited by examiner

SCREENING OF COMPOUNDS FOR TREATMENT OF ATHEROSCLEROSIS AND HEART ATTACK

This is a continuation in part of U.S. Ser. No. 09/606,324 filed Jun. 28, 2000, now U.S Pat. No. 6,437,215 which claims priority to U.S. Ser. No. 60/141,361 filed Jun. 28, 1999 and U.S. Ser. No. 60/164,679 filed Nov. 10, 1999.

STATEMENT REGARDING FEDERALLY SPONSORED RESEARCH

The U.S. government has certain rights to this invention by virtue of Grants HL41484, HI-52212, and HL20948 from the National Institutes of Health-National Heart, Lung and Blood Institute to Monty Kreiger and HL63609 and HL53793 to M. Simons and M. J. P. from the US National Institutes of Health.

BACKGROUND OF THE INVENTION

The present invention is generally in the area of transgenic animal models of atherosclerosis, methods for screening for inhibitors acting via interaction with the SR-BI scavenger receptor, and compositions obtained thereby.

The intercellular transport of lipids through the circulatory system requires the packaging of these hydrophobic molecules into water-soluble carriers, called lipoproteins, and the regulated targeting of these lipoproteins to appropriate tissues by receptor-mediated pathways. The most well characterized lipoprotein receptor is the LDL receptor, which binds to apolipoproteins B-100 (apoB-100) and E (apoE), which are constituents of low density lipoprotein (LDL), the principal cholesteryl-ester transporter in human plasma, very low-density lipoprotein (VLDL), a triglyceride-rich carrier synthesized by the liver, intermediate-density lipoprotein (IDL), and catabolized chylomicrons (dietary triglyceride-rich carriers).

All members of the LDL receptor gene family consist of the same basic structural motifs. Ligand-binding (complement-type) cysteine-rich repeats of approximately 40 amino acids are arranged in clusters (ligand-binding domains) that contain between two and eleven repeats. Ligand-binding domains are always followed by EGF-precursor homologous domains. In these domains, two EGF-like repeats are separated from a third EGF-repeat by a spacer region containing the YWTD motif. In LRP and gp330, EGF-precursor homologous domains are either followed by another ligand-binding domain or by a spacer region. The EGF-precursor homology domain, which precedes the plasma membrane, is separated from the single membrane-spanning segment either by an O-linked sugar domain (in the LDL receptor and VLDL receptor) or by one (in C. elegans and gp330) or six EGF-repeats (in LRP). The cytoplasmic tails contain between one and three "NPXY" internalization signals required for clustering of the receptors in coated pits. In a later compartment of the secretory pathway, LRP is cleaved within the eighth EGF-precursor homology domain. The two subunits LRP-515 and LRP-85 (indicated by the brackets) remain tightly and non-covalently associated. Only partial amino acid sequence of the vitellogenin receptor and of gp330 are available.

LDL receptors and most other mammalian cell-surface receptors that mediate binding and, in some cases, the endocytosis, adhesion, or signaling exhibit two common ligand-binding characteristics: high affinity and narrow specificity. However, two additional lipoprotein receptors have been identified which are characterized by high affinity and broad specificity: the macrophage scavenger receptors class A type I and type II.

Scavenger receptors mediate the binding of chemically modified lipoproteins, such as acetylated LDL (AcLDL) and oxidized LDL (OxLDL), and have been implicated in the pathogenesis of atherosclerosis (Krieger and Herz, 1994 Annu. Rev. Biochem. 63, 601-637; Brown and Goldstein, 1983 Annu. Rev. Biochem. 52, 223-261; Steinberg et al., 1989 N. Engl. J. Med. 320, 915-924). Macrophage scavenger receptors exhibit complex binding properties, including inhibition by a wide variety of polyanions, such as maleylated BSA (M-BSA) and certain polynucleotides and polysaccharides, as well as unusual ligand-cross competition (Freeman et al., 1991 Proc. Natl. Acad. Sci. U.S.A. 88, 4931-4935, Krieger and Herz, 1994). Several investigators have suggested that there may be at least three different classes of such receptors expressed on mammalian macrophages, including receptors which recognize either AcLDL or OxLDL, or both of these ligands (Sparrow et al., 1989 J. Biol. Chem. 264, 2599-2604; Arai et al., 1989 Biochem. Biophys. Res. Commun. 159, 1375-1382; Nagelkerke et al., 1983 J. Biol. Chem. 258, 12221-12227). The first macrophage scavenger receptors to be purified and cloned were the mammalian class A type I and II receptors. These are trimeric integral membrane glycoproteins whose extracellular domains have been predicted to include α-helical coiled-coil, collagenous and globular structures (Kodama et al., 1990 Nature 343, 531-535; Rohrer et al., 1990 Nature 343, 570-572; Krieger and Herz, 1994). The collagenous domain, shared by the class A type I and type II receptors, apparently mediates the binding of polyanionic ligands (Acton et al., 1993 J. Biol. Chem. 268, 3530-3537; Doi et al., 1993 J. Biol. Chem. 268, 2126-2133). The class A type I and type II molecules, which are the products of alternative splicing of a single gene, are hereafter designated class A scavenger receptors (SR-AI and SR-AII). The class A receptors, which bind both AcLDL and OxLDL (Freeman et al., 1991), have been proposed to be involved in host defense and cell adhesion, as well as atherogenesis (Freeman et al., 1991; Krieger, 1992 Trends Biochem. Sci. 17, 141-146; Fraser et al., 1993 Nature 364, 343-346; Krieger and Herz, 1994).

Based on models of the predicted quaternary structures of the class A type I and type II macrophage scavenger receptors, both contain six domains, of which the first five are identical: the N-terminal cytoplasmic region, the transmembrane region, spacer, α-helical coil, and collagen-like domains. The C-terminal sixth domain of the type I receptor is composed of an eight-residue spacer followed by a 102-amino acid cysteine-rich domain (SRCR), while the sixth domain of the type II receptor is only a short oligopeptide.

Using a murine macrophage cDNA library and a COS cell expression cloning technique, Endemann, Stanton and colleagues, (Endemann, et al. 1993 J. Biol. Chem. 268, 11811-11816; Stanton, et al. J. Biol. Chem. 267, 22446-22451), reported the cloning of cDNAs encoding two additional proteins that can bind OxLDL. The binding of OxLDL to these proteins was not inhibited by AcLDL. These proteins are FcgRII-B2 (an Fc receptor) (Stanton et al., 1992) and CD36 (Endemann et al., 1993). The significance of the binding of OxLDL to FcgRII-B2 in transfected COS cells is unclear because FcgRII-B2 in macrophages apparently does not contribute significantly to OxLDL binding (Stanton et al., 1992). However, CD36 may play a quantitatively significant role in OxLDL binding by macrophages (Endemann et al., 1993). In addition to binding oxidized LDL, CD36 binds thrombospondin (Asch et al., 1987 *J. Clin. Invest.* 79, 1054-1061), collagen (Tandon et al., 1989 *J. Biol. Chem.* 264, 7576-7583), long-chain fatty acids (Abumrad et al., 1993 *J. Biol. Chem.* 268, 17665-17668) and *Plasmodium falciparum* infected erythrocytes (Oquendo et al., 1989 *Cell* 58, 95-101). CD36 is expressed in a variety of tissues, including adipose, and in macrophages, epithelial cells, monocytes, endothelial cells, platelets, and a wide variety of cultured lines (Abumrad et al., 1993; and see Greenwalt et al., 1992 *Blood* 80, 1105-1115 for review). Although the physiologic functions of CD36 are not known, it may serve as an adhesion molecule due to its collagen-binding properties. It is also been proposed to be a long-chain fatty acid transporter (Abumrad et al., 1993) and a signal transduction molecule (Ockenhouse et al., 1989 *J. Clin. Invest.* 84, 468-475; Huang et al., 1991 *Proc. Natl. Acad. Sci. USA* 88, 7844-7848), and may serve as a receptor on macrophages for senescent neutrophils (Savill et al., 1991 *Chest* 99, 7 (suppl)).

Modified lipoprotein scavenger receptor activity has also been observed in endothelial cells (Arai et al., 1989; Nagelkerke et al., 1983; Brown and Goldstein, 1983; Goldstein et al., 1979 *Proc. Natl. Acad. Sci. U.S.A.* 76, 333-337). At least some of the endothelial cell activity apparently is not mediated by the class A scavenger receptors (Bickel et al., 1992 *J. Clin. Invest.* 90, 1450-1457; Arai et al., 1989; Nagelkerke et al., 1983; Via et al., 1992 *The Faseb J.* 6, A371), which are often expressed by macrophages (Naito et al., 1991 *Am. J. Pathol.* 139, 1411-1423; Krieger and Herz, 1994). In vivo and in vitro studies suggest that there may be scavenger receptor genes expressed in endothelial cells and macrophages which differ from both the class A scavenger receptors and CD36 (Haberland et al., 1986 *J. Clin. Inves.* 77, 681-689; Via et al., 1992; Sparrow et al., 1989; Horiuchi et al., 1985 *J. Biol. Chem.* 259, 53-56; Arai et al., 1989; and see below). Via, Dressel and colleagues (Ottnad et al., 1992 *Biochem J.* 281, 745-751) and Schnitzer et al. 1992 *J. Biol. Chem.* 267, 24544-24553) have detected scavenger receptor-like binding by relatively small membrane associated proteins of 15-86 kD. In addition, the LDL receptor related protein (LRP) has been shown to bind lipoprotein remnant particles and a wide variety of other macromolecules. Both the mRNA encoding LRP and the LRP protein are found in many tissues and cell types (Herz, et al., 1988 *EMBO J.* 7:4119-4127; Moestrup, et al., 1992 *Cell Tissue Res.* 269: 375-382), primarily the liver, the brain and the placenta. The predicted protein sequence of the LRP consists of a series of distinctive domains or structural motifs, which are also found in the LDL receptor.

As described by Kreiger, et al., in PCT/US95/07721 "*Class BI and CI Scavenger Receptors*" Massachusetts Institute of Technology ("Krieger, et al."), two distinct scavenger receptor type proteins having high affinity for modified lipoproteins and other ligands have been isolated, characterized and cloned. Hamster and murine homologs of SR-BI, an AcLDL and LDL binding scavenger receptor, which is distinct from the class A type I and type II macrophage scavenger receptors, has been isolated and characterized. In addition, DNA encoding the receptor cloned from a variant of Chinese Hamster Ovary Cells, designated Var-261, has been isolated and cloned. dSR-CI, a non-mammalian AcLDL binding scavenger receptor having high ligand affinity and broad specificity, was isolated from *Drosophila melanogaster.*

It was reported by Kreiger, et al. that the SR-BI receptor is expressed principally in steroidogenic tissues and liver and appears to mediate HDL-transfer and uptake of cholesterol. Competitive binding studies show that SR-BI binds LDL, modified LDL, negatively charged phospholipid, and HDL. Direct binding studies show that SR-BI expressed in mammalian cells (for example, a varient of CHO cells) binds HDL, without cellular degradation of the HDL-apoprotein, and lipid is accumulated within cells expressing the receptor. These studies indicate that SR-BI might play a major role in transfer of cholesterol from peripheral tissues, via HDL, into the liver and steroidogenic tissues, and that increased or decreased expression in the liver or other tissues may be useful in regulating uptake of cholesterol by cells expressing SR-BI, thereby decreasing levels in foam cells and deposition at sites involved in atherogenesis.

Atherosclerosis is the leading cause of death in western industrialized countries. The risk of developing atherosclerosis is directly related to plasma levels of LDL cholesterol and inversely related to HDL cholesterol levels. Over 20 years ago, the pivotal role of the LDL receptor in LDL metabolism was elucidated by Goldstein, et al., in the Metabolic and Molecular Bases of Inherited Disease, Scriver, et al. (McGraw-Hill, NY 1995), pp. 1981-2030. In contrast, the cellular mechanisms responsible for HDL metabolism are still not well defined. It is generally accepted that HDL is involved in the transport of cholesterol from extrahepatic tissues to the liver, a process known as reverse cholesterol transport, as described by Pieters, et al., *Biochim. Biophys. Acta* 1225, 125 (1994), and mediates the transport of cholesteryl ester to steroidogenic tissues for hormone synthesis, as described by Andersen and Dietschy, *J Biol. Chem.* 256, 7362 (1981). The mechanism by which HDL cholesterol is delivered to target cells differs from that of LDL. The receptor-mediated metabolism of LDL has been thoroughly described and involves cellular uptake and degradation of the entire particle. In contrast, the receptor-mediated HDL metabolism has not been understood as well. Unlike LDL, the protein components of HDL are not degraded in the process of transporting cholesterol to cells. Despite numerous attempts by many investigators, the cell-surface protein(s) that participate in the delivery of cholesterol from HDL to cells had not been identified before the discovery that SR-BI was an HDL receptor.

It is an object of the present invention to provide methods and reagents for designing drugs that can stimulate or inhibit the binding to and lipid movements mediated by SR-BI and redirect uptake and metabolism of lipids and cholesterol by cells.

It is another object of the present invention to provide methods and compounds for the treatment of atherosclerosis.

SUMMARY OF THE INVENTION

Transgenic animals that do not express functional SR-BI and ApoE develop severe atherosclerosis, by age four weeks in transgenic mice. Moreover, these animals exhibit progressive heart dysfunction starting by age four-six weeks, and die by age nine weeks. Pathology shows extensive fibrosis of the heart and occlusion of coronary arteries. The occlusion appears to be due to atherosclerosis, since fat deposition is in the walls. These animals are good models for the following diseases, and for screening of drugs useful in the treatment and/or prevention of these disorders: cardiac fibrosis, myocardial infarction, defects in electrical conductance, atherosclerosis, unstable plaque, and stroke. In contrast to other known models for atherosclerosis, these animals do not have to be fed extreme diets for long periods before developing atherosclerosis and heart dysfunction. No other known model for heart attacks and stroke with these characteristics is known.

This animal model has now been demonstrated to be useful as a screen for compounds which alleviate the symptoms of atherosclerosis and heart disease. Animals (Apo E−/−SR-BI+/−) were fed PROBUCOL beginning at the time of mating. Offspring are weaned at three weeks and fed PROBUCOL. In contrast to animals not fed PROBUCOL, 50% of whom are dead at six weeks, all animals on PROBUCOL have a normal phenotype (MRI of heart function, ECG, echocardiogram, histology) at six weeks. At seven to eight months, there is evidence of atherosclerosis and some myocardial infarction. This demonstrates that the compound has a preventative action. Animals who are taken off of the PROBUCOL all die within ten to twelve weeks. In another study, the majority of animals whose parents were not fed PROBUCOL, but who received the PROBUCOL beginning before five weeks of age, survived for a few months, demonstrating that the compound also has a therapeutic benefit. The earlier the treatment with PROBUCOL, the longer the survival of the animals.

DETAILED DESCRIPTION OF THE INVENTION

The role of SR-BI has now been confirmed as the principle mediator of cholesteryl ester transport from peripheral tissues to the liver and other steroidogenic tissues, including the adrenal gland, testes and ovaries. The studies described herein demonstrate that animals which are deficient in both SR-BI and ApoE are not only excellent models for atherosclerosis but also myocardial infarction and stroke, since the animals develop progressive heart dysfunction and coronary artery occlusions characterized by plaques resembling those in heart attack patients.

These animals can be used to screen for drugs that are effective as therapeutics or diagnostics of heart disease as demonstrated in the examples. As also demonstrated by the examples, compounds have been identified as useful in treating or preventing atherosclerosis or heart attack in individuals having deficiencies in SR-BI.

Pharmaceutical Compounds

A number of compounds are useful in altering lipid levels and cholesterol metabolism. A preferred class of compounds are PROBUCOL (4,4'-(isopropylidenedithio) bis(2,6-di-tert-butylphenol)) and monoesters of PROBUCOL, for example, as described in U.S. Pat. No. 6,121,319 to Somers and other derivatives as described by FR 2168137, FR 2140771, FR 2140769, FR 2134810, FR 2133024, and FR 2130975. These compounds have potent antioxidant properties and block oxidative modification of LDL. PROBUCOL has two known effects: (1) hypocholesterolemic agent (reduces plasma cholesterol, HDL and LDL in humans—side effect, causes long QT syndrome, which their esters avoid, as well as decrease in HDL) and (2) an antioxident, may also play a role in fertility.

Another useful compound available from Chugai of Japan is BO 653, 2,3-Dihydro-5-hydroxy-2,2-dipentyl-4,6-di-tert-butyl-benzofuran, an antioxident. Noguchi, et al., Arch. Biochem. Biophys. 1:347 (1997).

Based on the PROBUCOL data, other compounds that will be effective include other hypocholesterolemic and antioxident compounds, including vitamin E and vitamin C, as fertility enhancing agents as well as for treatment and/or prevention of cardiovascular disease or atherosclerosis. The preferred compounds would have both activities.

Pharmaceutical Compositions

Compounds are preferably administered in a pharmaceutically acceptable vehicle. Suitable pharmaceutical vehicles are known to those skilled in the art. For parenteral administration, the compound will usually be dissolved or suspended in sterile water or saline. For enteral administration, the-compound will be incorporated into an inert carrier in tablet, liquid, or capsular form. Suitable carriers may be starches or sugars and include lubricants, flavorings, binders, and other materials of the same nature.

Alternatively, the compound may be administered in liposomes or microspheres (or microparticles). Methods for preparing liposomes and microspheres for administration to a patient are known to those skilled in the art. U.S. Pat. No. 4,789,734 describe methods for encapsulating biological materials in liposomes. Essentially, the material is dissolved in an aqueous solution, the appropriate phospholipids and lipids added, along with surfactants if required, and the material dialyzed or sonicated, as necessary. A review of known methods is by G. Gregoriadis, Chapter 14. "Liposomes", *Drug Carriers in Biology and Medicine* pp. 287-341 (Academic Press, 1979). Microspheres formed of polymers or proteins are well known to those skilled in the art, and can be tailored for passage through the gastrointestinal tract directly into the bloodstream. Alternatively, the compound can be incorporated and the microspheres, or composite of microspheres, implanted for slow release over a period of time, ranging from days to months. See, for example, U.S. Pat. Nos. 4,906,474, 4,925,673, and 3,625,214.

The pharmaceutical compositions are administered in an effective amount effective to modify or treat the disorder. These are readily determined by measuring blood, urine and/or tissue samples using clinically available tests, as demonstrated below.

The present invention will be further understood by reference to the following non-limiting examples.

EXAMPLE 1

Production and Characterization of Transgenic Animals that do not Express SR-BI To determine directly if SR-BI normally plays an important role in HDL metabolism in vivo and to establish an experimental system to examine the role of SR-BI in pathologic states, mice containing a targeted null mutation in the gene encoding SR-BI were generated.

Materials and Methods

Generation of SR-BI Mutant Mice

SR-BI genomic DNA was isolated from a mouse strain 129 DNA library (Genome Systems, St. Louis, Mo.), and screened by PCR amplification using primer pairs corresponding to the 5' and 3' ends of the mSR-BI cDNA. From one clone a 12 kb Xba I fragment containing the first coding exon was identified. A replacement-type targeting vector, containing 0.75 kb and 9 kb short and long homology regions and the po12sneobpA and herpes simplex virus thymidine kinase (TK) cassettes, was constructed using standard methods. The vector was linearized and 100 μg were transfected by electroporation (240 V, 500 μF) into 112×10$^6$ murine D3 embryonic stem cells, which were then plated onto irradiated mouse embryonic fibroblast feeder layers. After G418/gancyclovir positive/negative selection for 7-8 days, 492 of the 5800 surviving colonies were picked and screened by PCR analysis using primers specific for the targeted allele (primer 1 5'-TGAAGGTGGTCTTCAAGAG-CAGTCCT-3' (SEQ ID NO:1); and primer 3 5'-GATTGG-GAAGACAATAGCAGGCATGC-3' (SEQ ID NO:2); all oligonucleotide primers were synthesized by Research Genetics). The presence of the targeted allele (amplification of a 1.4 kb band) was confirmed by Southern blot analysis of Xba I digested genomic DNA using probes that yielded either the predicted 12 kb fragment characteristic of the wild-type allele or the predicted 2.5 kb and 9 kb fragments from the targeted mutant allele. Bam HI digested genomic DNA was also probed with a 0.9 kb fragment derived by Pst I digestion of the neomycin resistance gene cassette to confirm the presence of a single neo gene in the mutant cells. Embryonic stem cell clones containing a disrupted SR-BI allele were injected into C57BL/6 blastocysts, which were implanted into recipient females. The resulting chimeric mice were crossed to C57BL/6 female mice to generate F1 wild-type (srbI$^{+/+}$) and heterozygous (srbI+/$^{+-}$) mice on an identical 129 (agouti)/C57BL/6 background. F1 heterozygotes were crossed to generate F2 wild-type (srbI$^{+/+}$), heterozygous mutant (srbI$^{+/-}$) and homozygous mutant (srbI$^{+/-}$) progeny. The presence of the targeted or wild-type SR-BI alleles in DNA extracted from tail biopsies was detected by PCR amplification using primer 1 (SEQ ID NO: 1) in combination with either primer 3 (SEQ ID NO:2) (mutant specific) or primer 2 (wild-type specific; 5'-TATCCTCG-GCAGACCTGAGTCGTGT-3' (SEQ ID NO:3)). Genotypes were confirmed by Southern blot analysis. Mice were housed in microisolator cages and were fed ad libitum a regular rodent chow diet (Prolab 3000, PMI Feeds Inc., St. Louis, Mo.).

Analysis of Animal Tissues

Samples were obtained from fasted (4-8 hrs) or non-fasted mice that were approximately 8-12 weeks old (F1 generation) or 5-11 weeks old (F2 generation).

Immunoblot Analysis

Animals were sacrificed and livers and adrenal glands were removed and immediately frozen. Membranes from homogenates were prepared. 50 µg of protein per specimen were analyzed by SDS-polyacrylamide (8%) gel electrophoresis and immunoblotting with chemiluminescence detection as previously described using rabbit antipeptide polyclonal antibodies which specifically recognize either the approximately 82 kDa murine SR-BI protein (anti-mSR-BI$^{485}$) or the approximately 36 kDa ε-COP control cytoplasmic protein (anti-εCOP).

Plasma and Adrenal Cholesterol Analysis

Plasma total cholesterol (unesterified plus esterified, mg/dl) was measured using an enzymatic kit (Sigma Chemicals, St. Louis, Mo.). Adrenal glands were homogenized as described above. Protein concentrations in the homogenates were measured using the method of Lowry et al. Duplicate samples of homogenates (30-70 µl each) were extracted with 2 ml of hexane/isopropanol (2:1) for 1 h at room temperature, back-washed with 1 ml of water, and phases separated by centrifugation at 800× g for 5 min. The upper organic phase was recovered and evaporated at 37° C. in a Speedvac concentrator and cholesterol was measured in the dried pellet using an enzymatic kit (Sigma). Cholesterol values were corrected based on the recovery of a [$^3$H]cholesteryl ester internal standard added prior to lipid extraction. Total cholesterol content was expressed as µg of cholesterol/mg total protein.

Lipoprotein Analysis

Pooled plasma (150 µl total from 2-6 animals) was diluted with an equal volume of elution buffer (154 mM NaCl 1 mM EDTA, pH 8) and subjected to FPLC using two Superose 6 columns (Pharmacia, Piscataway, N.J.) connected in series. Proteins were eluted at 0.25 ml/min. Forty seven fractions (0.5 ml) were collected after the first 14 ml were eluted and total cholesterol in each fraction was determined as described above. Immunoblotting of the FPLC fractions was performed with specific anti-apoA-I, anti-apoA-II or anti-apoE antibodies on independent samples or by sequential labeling of a single membrane to permit simultaneous visualization of all three proteins.

Statistical Analysis

Results are expressed as the arithmetic mean ± standard deviation. The statistical significance of the differences of the mean between groups was evaluated using the Student t test for unpaired comparisons. The $\chi^2$ test was used for genotype distribution analysis. P values <0.05 are considered to be statistically significant.

Results and Discussion

The SR-BI gene was inactivated in embryonic stem cells by standard homologous recombination methods. The segments replaced in the recombined mutant ("Targeted Allele") include the entire coding region of the first coding exon (126 bp, 42 amino acids, containing 5' untranslated sequence, a short N-terminal cytoplasmic domain, and a portion of the N-terminal putative transmembrane domain that probably also functions as an uncleaved leader sequence for insertion into the ER during biogenesis) and an additional 554 bases of the adjacent downstream intron. The mutated locus is expected to encode a transcript which would not be translated or would be translated into nonfunctional, non-membranous, and presumably unstable, protein. Two sets of primer pairs specific for the wild-type (primers 1 and 2) (SEQ ID NO:1 and SEQ ID NO:3 respectively) or targeted mutant (primers 1 and 3) (SEQ ID NO:1 and SEQ ID NO:2 respectively) alleles were used to screen genomic DNA by PCR as described in heterozygous and F2 homozygous mutant animals are shown. Immunoblot analysis of hepatic membranes (50 µg protein/lane) from unfasted wild-type (F1 and F2 generations), heterozygous (F1 and F2 generations) and homozygous mutant (F2 generation) male mice were performed using polyclonal antipeptide antibodies to SR-BI (approximately 82 kDa, top) or the internal control ε-COP (approximately 36 kDa). Essentially identical results were obtained using specimens from female mice) confirmation of the expected null mutation by PCR.

Three independently derived embryonic stem cell clones containing the targeted allele were injected into C57BL/6 blastocysts and two produced 24 male chimeras, of which 11 gave germ line transmission of the targeted SR-BI allele when crossed to c57BL/6 females. F1 offspring were either homozygous (+/+) for the wild type allele or heterozygous (+/−) with both mutant and wild-type PCR products. F1 heterozygotes should be isogenic with the F1 wild-type controls except at the SR-BI locus. Wild-type, heterozygous and homozygous mutant F2 generation offspring, whose phenotypes are subject to genetic background variability, were generated from F1 intercrosses. In the F2 progeny analyzed to date (n=317), the observed ratios of wild-type heterozygous mutant homozygous mutant offspring were 1.0:1.7:0.5, values significantly different from the expected Mendelian ratio of 1:2:1 (p=0.003). Thus, there may be partially penetrant effects of the mutation either on neonatal survival or on embryonic development, which would be consistent with the distribution of SR-BI on the maternal surfaces of cells in the placenta and yolk sac during embryonic development.

All of the mutants looked normal (weight, general appearance and behavior) and the males were fertile. No offspring from female homozygous mutants have been obtained following multiple attempts to do so, indicating a substantial, and possibly complete, decrease in fertility in these females. Immunoblot analysis of liver membranes from F1 (+/+,+/−) and F2 (+/+,+/−,−/−) mice using anti-peptide antibodies which recognize the C-terminus of the SR-BI protein (anti-mSR-BI$^{495}$), or a segment of the putative extracellular loop (anti-mSR-BI$^{230}$), revealed that there was about half as much mSR-BI protein in the heterozygous mutants as in the wild-type controls and no detectable SR-BI in the homozygous mutants. No fragment or other variants of the full-length protein were detected in any of the samples. In contrast, no significant differences were observed in the levels of the control protein, $\epsilon$-COP. Similar results were observed using adrenal tissue. Thus, the mutated SR-BI gene is a functionally null allele.

To determine how decreased SR-BI protein expression influenced lipoprotein metabolism, the plasma cholesterol levels in male and female wild-type and mutant mice were compared. Because there were no statistically significant differences between the data from animals derived from the two independent embryonic stem cell clones, data from these two independent sets of animals were pooled. Relative to wild-type controls there were statistically significant increases in the plasma total cholesterol concentrations of approximately 30-40% in F1 and F2 heterozygotes and 2.2-fold in F2 homozygous mutants. In contrast to the increased plasma cholesterol in the mutants, there was no statistically significant change in the levels of plasma apoA-I. These findings are consistent with the suggestion that hepatic SR-BI plays a key role in selective removal of cholesterol from circulating HDL-lower levels of hepatic SR-BI were expected to increase plasma HDL cholesterol but not directly alter apoA-I levels.

To determine if the elevated levels of plasma cholesterol in the mutants were due to changes in HDL, pooled plasma samples from F1 male and female and F2 male animals were subjected to FPLC and the total cholesterol content as well as the relative amounts of apoA-I, apoA-II and apoE in each fraction were measured. For wild-type mice (srbI$^{+/+}$) most of the cholesterol, apoA-I and apoA-II were in the HDL fraction, with small or undetectable amounts in the VLDL and IDL/LDL fractions. There was an apparently low level of apoE which both co-migrated with the HDL and with a small cholesterol peak in the IDL/LDL region. The cholesterol and apolipoprotein profiles of the heterozygous mutants were similar to those of the wild-type controls, except that there was an increase in the amount of cholesterol in the HDL fractions and there was a tendency of the HDL peak (cholesterol and/or apolipoproteins) to be broader than that of wild-type and shifted slightly to the left, which may represent large HDL particles. This suggested that there might be a difference in the average sizes of the HDL particles due to the inactivation of one of the SR-BI alleles; however, this shift was not observed in all specimens. In the F2 homozygous mutant animals (srbI$^{-/-}$) the cholesterol was found in a large, somewhat heterogeneous peak in the HDL range, but shifted to the left (larger apparent size) of the wild-type HDL peak. The amount of cholesterol in the IDL/LDL fraction varied between samples.

Combined immunoblot analysis of fractions 23-28 from the chromatograms were performed with polyclonal antibodies to apoE, apoA-I and apoAII. Additional analysis of these and independent chromatograms established that there were no additional peaks containing apoA-I in fractions containing larger lipoproteins (fractions 1-22) and that the only other peak containing a small amount of apoE was in fraction 6, which corresponds to VLDL. The distributions of apoA-I and apoA-II were similar to that of cholesterol, although, unlike the case for apoA-I there was a notable reduction in the amount of apoA-II relative to that seen in wild type and heterozygous mutant animals. Conversely, in the homozygous mutants there was a substantial increase in the amount of apoE, whose distribution profile (larger particles, centered around fractions 26-28) differed from, but overlapped, those of apoA-I and apoA-II.

These results with the mutant animals, in which the changes in SR-BI expression are in the physiologic range, are complementary to and consistent with the observation that transient adenovirus-mediated hepatic SR-BI overexpression results in dramatically decreased levels of HDL cholesterol and increased delivery of HDL-associated lipid to hepatocytes and the bile. In rodents, most of the plasma HDL cholesterol appears to be removed by the liver via selective uptake and the liver appears to be the site of the highest total amount of SR-BI protein expression. It seems likely that buildup of large, cholesterol-enriched lipoprotein particles in the circulation of SR-BI mutants was primarily due to decreased hepatic selective HDL cholesterol uptake. Thus, it appears that murine plasma HDL cholesterol levels are particularly sensitive to physiologically relevant changes in the levels of hepatic SR-BI protein expression (e.g., approximately 50% reduction in heterozygotes). The effect of the null mutation in SR-BI on total plasma cholesterol levels was quantitatively similar to that of a null mutation in the LDL receptor. For both sets of mutants, total plasma cholesterol levels were approximately 36% above wild-type controls for heterozygotes and approximately 114% for homozygotes. It is important to emphasize that while the magnitudes of the effects on total plasma cholesterol of these distinct mutations (SR-BI vs. LDL receptor) are similar, the mechanistic consequences on lipoprotein metabolism (e.g., effects on the various lipoproteins) differ.

In addition to playing an important role in regulating plasma HDL cholesterol, SR-BI has been implicated in the delivery of HDL cholesterol to the adrenal gland and other steroidogenic tissues, both for the accumulation of esterified cholesterol stores and for steroid hormone synthesis. To examine this, the cholesterol content of adrenal glands in mutant and wild-type mice was measured. The results are shown in Table 1. As predicted, cholesterol stores in the adrenal gland dropped substantially in the heterozygous and homozygous mutants to 58% and 28% of control, respectively. It was also noted that the color of intact adrenal glands from homozygous mutants was brownish-red while that of wild-type and heterozygous animals was light yellow and, in preliminary studies, a dramatic decrease in oil red O staining of the adrenal cortex was observed in the homozygous mutants relative to the wild-type mice. Thus, the total cholesterol content, color and oil red O staining characteristics of the adrenal glands in SR-BI homozygous mutants resembled those in their cholesterol-depleted counterparts in other murine mutants, including null mutants in the SR-BI ligand apoA-I. This similarity with apoA-I knockouts is consistent with the possibility that the reduction in adrenal cholesterol in the SR-BI homozygotes is a direct consequence of the loss of the key receptor for selective lipid uptake. Recent antibody blocking experiments have provided additional support for a major role of mSR-BI in delivering HDL cholesterol to cultured adrenocortical cells for steroidogenesis. Based on the tissue distribution and hormonal regulation of SR-BI protein expression and the phenotypes of apoA-I knockouts, it seems likely that there would also be reductions in cholesterol stores in other steroidogenic tissues (e.g., ovary, testes) in SR-BI homozygous mutants. Adrenal cholesterol deficiency in both the apoA-I and SR-BI homozygous mutants also suggests that LDL receptors in the mouse, in which there normally is little LDL in the plasma, do not normally contribute significantly to murine adrenal cholesterol accumulation.

cholesterolemic animals developed significant atherosclerotic lesions in the aortic sinus as early as 4 to 5 weeks after birth. They also exhibited extensive lipid-rich coronary artery occlusions and spontaneously developed multiple myocardial infarctions and cardiac dysfunction (eg, enlarged hearts, reduced ejection fraction and contractility, and ECG abnormalities). Their coronary arterial lesions, which were strikingly similar to human atherosclerotic plaques, exhibited evidence of cholesterol clefts and extensive fibrin deposition, indicating hemorrhage and clotting. All of the dKO mice died by 8 weeks of age (50% mortality at 6 weeks). Thus, SR-BI/apoE dKO mice provide a murine model for CHD and may help better define the role of lipoprotein metabolism and atherosclerosis in the pathogenesis of myocardial infarction and cardiac dysfunction. Furthermore, these animals are useful for preclinical testing of potential genetic and/or pharmacological therapies for CHD.

Materials and Methods

Animals

Mice (mixed C57BL/6×129 background) were generated at MIT and were housed and fed a normal chow diet. Unless otherwise noted, 4- to 6-week old dKO mice, apoE KO

TABLE I

Effects of SR-BI Gene Disruption on Plasma Total Cholesterol and Apo A-I Concentrations, and Adrenal Gland Total Cholesterol Content in Wild-type (srbI$^{+/+}$), Heterozygous (srbI$^{+/-}$), and Homozygous (srbI$^{-/-}$) Mutant Mice.

| srbI genotype | gender | F1 Generation Plasma Total Cholesterol | | Plasma Total Cholesterol | | F2 Generation$^≞$ Plasma ApoA-1 | | Adrenal Gland Total Cholesterol | |
|---|---|---|---|---|---|---|---|---|---|
| | | mg/dl | % of control | mg/dl | % of control | mg/dl | % of control | μ/mg protein | % of control |
| +/+ | Male | 93 ± 8(29) | 100 | 99 ± 12(18) | 100 | — | — | — | — |
| | Female | 80 ± 7(13) | 100 | 94 ± 20(27) | 100 | — | — | — | — |
| | Both | 89 ± 10(42) | 100 | 96 ± 17(45) | 100 | 25 ± 3(10) | 100 | 128 ± 28(5) | 100 |
| +/− | male | 126 ± 10(21) | 100 | 137 ± 21(29) | 100 | — | — | — | — |
| | female | 112 ± 9(23) | 140 | 118 ± 9(49) | 112 | — | — | — | — |
| | Both | 126 ± 12(44) | 134 | 126 ± 22(78) | 131 | 28 ± 2(12) | 112 | 74 ± 18(6) | 58 |
| −/− | male | — | — | 220 ± 41(10) | 222 | — | — | — | — |
| | female | — | — | 209 ± 32(7) | 222 | — | — | — | — |
| | Both | — | — | 216 ± 37(17) | 225 | 27 ± 3(11) | — | 36 ± 7(5) | 28 |

Values for F1 generation represent mean ± standard deviation. Values for F2 generation in parenthesis represent the numbers of animals analyzed. Values for plasma total cholesterol determined with an Autoanalyzer and human apoA-I standards. F1 generation animals were not fasted. F2 generation animals were not fasted prior to analysis of adrenal gland cholesterol levels but were fasted for 4-8 h prior to analysis of plasma.

EXAMPLE 2

Loss of SR-BI Expression Leads to the Early Onset of Occlusive Atherosclerotic Coronary Artery Disease, Spontaneous Myocardial Infarctions, Severe Cardiac Dysfunction, and Premature Death in Apolipoprotein E-Deficient Mice Murine models of atherosclerosis, such as the apolipoprotein E (apoE) or the LDL receptor knockout mice, usually do not exhibit many of the cardinal features of human coronary heart disease (CHD), eg, spontaneous myocardial infarction, severe cardiac dysfunction, and premature death. Mice with homozygous null mutations in the genes for both the high density lipoprotein receptor SR-BI and apoE (SR-BI/apoE double knockout [dKO] mice) exhibit morphological and functional defects with similarities to those seen in human CHD. When fed a standard chow diet, these hyperlittermates, and SR-BI KO and wild type controls on the same background were studied. No significant differences were observed between males and females.

Histology

Mice were euthanized and tissues prepared for cryosectioning. Tissues for paraffin sections were immersion fixed in buffered 10% formalin (J. T. Baker). Sometimes heparin was administered (450 U/20 g, IV) prior to euthanasia to prevent coagulation. Tissue sections were stained with Masson's trichrome (Sigma), hematoxylin, and eosin (H&E) or Oil red O and hematoxylin. Immunohistochemistry was performed using anti-fibrin (NYB-T2G1, 1 _g/mL, Accurate Chemical & Scientific Corp) or anti-macrophage (F4/80, MCA 497, Serotec, diluted 1:10) antibodies using M.O.M. immunodetection (AEC substrate) or Vectastain Elite ABC (diaminobenzidine substrate) kits (Vector), respectively, with hematoxylin counter-staining.

Gravimetry

Mice were euthanized, weighed, and perfused, and intact hearts or the right ventricular (RV) free wall and the left ventricle (LV)_septum (LV_S) were dissected and weighed.

Magnetic Resonance Imaging (MRI)

Mice were anesthetized (chloral hydrate, 200 to 320 mg/kg IP; Sigma) and placed in a 2T small bore magnet (Bruker Instruments) on a custom body coil containing ECG electrode patches. Heart rates were adjusted to approximately 300 bpm with 1% to 2% isoflurane. Scout, long-axis, and 6 to 7 1-mm thick short-axis images were collected. Short-axis images spanning the entire heart were used to measure LV tissue volume, LV end diastolic and end systolic luminal volumes (LVEDV and LVESV), and ejection fractions (EF_((LVEDV_LVESV)/LVEDV)_100%).

Hemodynamic Evaluation

Mice were heparinized (1 U/10 g IP), anesthetized with chloral hydrate as above, intubated, and ventilated (Harvard Apparatus, Inc) with room air (130 breaths/min; tidal volume: approximately 15 µL/g). Lidocaine HCL (0.5%; Abbott) was administered locally. The right carotid artery was exposed and a 1.4 Fr micromanometer catheter (Millar Instruments) was advanced into the aorta and then the LV for pressure measurements. LV pressures were measured before and after cutting both vagal nerves. Data were recorded using a Windaq DI 220 converter and analyzed using Windaq Pro software (Dataq Instrument) with some manual intervention to correct for micromanometer drift and insure proper evaluation of LVEDP.

Angiography

After median sternotomy, cannulation of the ascending aorta (PE50 polyethylene tubing: Becton Dickinson and Company), and opening the right atrium for drainage, each heart was harvested, flushed with PBS, and barium sulfate (E-Z-EM, Inc) was injected manually at a maximum pressure of 80 mm Hg. Angiograms were obtained with a Micro 50 (General Electric, 20 kV, 20-second exposure). Only the left coronary arterial network could be routinely observed.

Electrocardiography

For avertin-anesthetized mice, ECGs were recorded using 6 standard limb leads with a Silogic EC-60 monitor (Silogic Design Limited). For conscious mice, ECGs were recorded using AnonyMOUSE ECG Screening Tools (Mouse Specifics, Inc).

Statistical Analysis

A value of P<0.05 was considered significant (2-tailed, unpaired Student's t test or ANOVA test, StatView).

Results

SR-BI/apoE double KO mice (dKO mice) fed a standard low fat/low cholesterol diet develop extensive aortic sinus atherosclerosis by 5 weeks of age and die prematurely. All of the dKO mice died between 5 to 8 weeks of age (50% mortality at 6 weeks). No control mice died during this period. Before death, the dKO mice exhibited a 1- to 2-day period of progressively reduced activity and altered appearance (ruffled fur, abnormal gate, and occasionally labored breathing).

Extensive Myocardial Fibrosis dKO hearts were enlarged relative to controls (eg, apoE KO) and exhibited pale, discolored patches not seen in any controls, suggesting extensive MI and scarring. These lesions were always present in the atrioventricular (AV) groove of the left ventricle and frequently present at various locations on the right ventricular (RV) wall, the LV wall, and/or the apex. Regions surrounding the mitral valves (not the valves themselves) and the LV outflow tract were invariably fibrotic. Higher magnification views and show lesions contained fibrotic connective tissue, few remaining myocytes, and numerous large, dilated, apparently mononuclear inflammatory cells, some of which were macrophages. Lesions in the RV free wall and more apical regions appeared more well-organized and contained fewer dilated cells than those in the outflow tract area and were characterized by extensive fibrosis, inflammation, and in some cases, diffuse necrosis and myocardial scarring typical of healed infarcts. Numerous macrophages were detected in these lesions and lesions in the papillary muscle. Thus, macroscopic and microscopic observations revealed multiple MIs in the dKO mice. In hypercholesterolemic animals, macrophages can accumulate extensive cytosolic lipid deposits (foam cells). Neutral lipid staining (oil red O) of dKO hearts was particularly intense in macrophage-rich, fibrotic regions and appeared both in a concentrated, intense, globular pattern reminiscent of intracellular lipid and in a punctate pattern reminiscent of extracellular lipid. More diffusely distributed lipid was detected in non-fibrotic tissue throughout the heart between myocardial fibers. The codistribution of lipid and macrophages suggested the presence of macrophage foam cells. Future studies will determine if macrophage infiltration into fibrotic lesions is a consequence of and/or contributes to lesion development and if these lesions are similar to those in human inflammatory cardiomyopathies.

Heart Function

Intact hearts and LVs_septa (LV_S) and RVs from dKO mice were larger than those from age-matched controls (1.6- to 1.8-fold greater mean heart-to-body weight ratios). Furthermore, dKO mice had a significantly lower body weight (15.3:2.0 g) than control animals (wild type: 20.7:4.3 g; SR-BI KO: 21.3:3.8 g; apoE KO: 18.8:2.3 g. P<0.002). This was confirmed by MRI analysis of LV_S tissue volume. Increased tissue volume reflects a thicker LV_S wall (assuming no change in ventricular length). In contrast, the body weight-corrected LVEDVs were only slightly higher for dKO hearts, suggesting only minor dilation. Thus, the increased size of dKO hearts was due primarily to increased ventricular tissue mass, possibly resulting from thickening of the wall near the outflow tract and compensatory thickening of the ventricular wall in response to reduced contractility. Hemodynamic analysis revealed that aortic systolic blood pressure and heart rate (HR) were significantly lower in dKO than in control mice. dKO mice also had substantially lower LV systolic pressure (LVSP) and contractility (_dP/dt), indicating LV systolic dysfunction. A similar (3-fold) reduction in _dP/dt indicated impaired LV relaxation. The somewhat lower HR of dKO mice relative to controls (not observed in non-anesthetized mice) was not due to extracardiac neuronal influences (bilateral disruption of the vagal nerves did not eliminate the HR differences). Although reduced HR might have contributed to reduced blood pressure and contractility, and might complicate interpretation of differences in dP/dt values, it is unlikely that these relatively small baseline differences caused the large changes in both _dP/dt and _dP/dt. Furthermore, values for the products of pressures (P) with either _dP/dt or _dP/dt showed the same trends, indicating a minimal or insignificant influence of pressure on dP/dt values. The decreased aortic blood pressures and abnormal contractility and relaxation in these dKO mice are consistent with primary cardiac dysfunction. Carotid arterial blood pressure was measured in dKO mice (n=3) and control littermates (apoE KO mice with a heterozygous null mutation in SR-BI, n=3) at 3 (chloral hydrate anesthesia, 0.2 mg/g) and again at 4 (urethane anesthesia, 1 mg/g) weeks of age. No blood pressure differences at 3 weeks and only a slight relative reduction in the dKO mice at 4 weeks. Thus, it is unlikely that hypertension was responsible for the ventricular hypertrophy or other cardiac defects exhibited by dKO animals. MRI images at end-diastole or end-systole show that, whereas the LVEDVs were similar, the LV end systolic volumes (LVESVs) were substantially higher in dKO hearts than in the controls. Consequently, the ejection fractions of the dKO hearts, a critical measure of heart function, were substantially lower (approximately 50%) than those of controls. In unanesthetized, conscious mice, normal ECG patterns were seen in controls, whereas striking abnormalities were observed in 6 of 12 dKO mice. One exhibited an ST elevation of unclear etiology, and 5 showed severe ST depression, indicating subendocardial ischemia. 14,16 In 5 of 8 dKO mice, but not in any controls.

age-matched controls. A partially cellular, lipid-rich lesion almost completely occludes the lumen of a left coronary branching artery. Fibrosis and inflammatory cells surrounding an occluded artery in the RV wall of another dKO mouse. Proximal lesions in coronary ostia were also seen in 7 of 10 dKO mice. These complex lesions are probably responsible for the patchy MIs in the LV and RV. Serial cross-sections through an occluded coronary artery from another dKO mouse. Trichrome and lipid staining revealed numerous cholesterol clefts within a lipid-rich, acellular, potentially 'necrotic' core. Frequently, a substantial portion of the lesions appeared to be acellular, and some of these amorphous regions stained blue with trichrome, suggesting the presence of collagen. Immunostaining showed fibrin deposits in the core regions of 8 of 10 lesions observed in 3 of 3 dKO mice but not in age-matched apoE KO controls (n=3). This thrombosis may be a consequence of bleeding into these complex lesions or perhaps plaque rupture.

The severe occlusive, fibrin-containing coronary arterial lesions, probable ischemia, multiple MIs, enlarged hearts, and cardiac dysfunction in very young (approximately 5 weeks old), low-fat/low-cholesterol fed SR-BI/apoE dKO mice provide a model of CHD. Combined deficiencies of SR-BI and apoE profoundly alter lipoprotein metabolism, 9 resulting in decreased biliary cholesterol and increased plasma cholesterol. The molecular mechanisms responsible for the dramatically accelerated occlusive atherosclerotic disease in the dKO mice relative to the apoE KO mice may include (1) changes in plasma proatherogenic and anti-atherogenic lipoproteins, (2) altered cholesterol flux into or out of the artery wall, and (3) decreased RCT. SR-BI has also recently been shown to mediate HDL-dependent endothelial nitric oxide synthetase activation in vascular endothelium and the cellular uptake from lipoproteins of vitamin E, which can inhibit atherosclerosis in apoE KO mice.30-32 Loss of these activities may contribute to the accelerated

TABLE II

Hemodynamic Analyses of Heart Function in Control and dKO Mice

| Genotype | Aortic Diastolic Pressure, mm Hg | Aortic Systolic Pressure, mm Hg | LVEDP, mm Hg | LVSP, Mm Hg | +dP/dt, Mm Hg/s | −dP/dt, mm Hg/s | Heart Rate, bpm |
|---|---|---|---|---|---|---|---|
| Wild type | 61 ± 17(6) | 86 ± 17(6) | 5.7 ± 0.9(6) | 88 ± 17(6) | 3800 ± 900(6) | −3400 ± 800(6) | 509 ± 71(6) |
| SR-BI KO | 55 ± 22(5) | 79 ± 20(5) | 7 ± 4.4(3) | 73 ± 11(3) | 3200 ± 900(3) | −2900 ± 600(3) | 565 ± 122(5) |
| ApoE KO | 52 ± 12(5) | 77 ± 9(5) | 6.1 ± 1.7(5) | 82 ± 7(5) | 3500 ± 500(5) | −3300 ± 500(5) | 524 ± 77(5) |
| DKO | 39 ± 6(6) | 54 ± 5(6)† | 9.6 ± 2.2(6) | 40 ± 19(6)† | 1100 ± 500(6)‡ | −1100 ± 400(6)‡ | 390 ± 39(6) |
| P(ANOVA)* | 0.1 | 0.005 | 0.49 | 0.0002 | <0.0001 | <0.0001 | 0.01 |

Data shown here were obtained before cutting the vagal nerves (see Materials and Methods). LVEDP indicates LV and diastolic pressure; LVSP, LV systolic pressure. Values represent mean_1 SD. Numbers of animals per group are indicated in parentheses.
*ANOVA test of probability that all samples belong to the same group.
†, ‡Pairwise comparisons with each of the controls by unpaired Student's t test; †P_0.03 and ‡P_0.003.

To determine if occlusive coronary artery disease may have contributed to cardiac dysfunction, ex vivo angiography was performed. No obvious defects were apparent in control hearts (wild type, n=4; apoE KO, n=4, and SR-BI KO, n=3). Five of seven dKO hearts examined showed stenoses and occlusions of branches of the left coronary arteries, and there were two instances of apparent stenoses in the main coronary arteries. Histological analyses of dKO hearts revealed extensive coronary artery disease (CAD). There were complex occlusions of major arterial branches in the LV free wall (9 of 10 mice analyzed), the septum (10 of 11), and the RV wall (11 of 12). No occlusions were seen in atherosclerosis in dKO mice. The occlusive lesions in coronary arteries of SR-BI/apoE dKO mice were highly complex, containing cholesterol clefts and fibrin deposits. The occlusive lesions in SR-BI/apoE dKO mice apparently result in ischemia and the formation of multiple patchy MIs with variable sizes and locations. In humans, multiple infarcts lead to a gradual decline in systolic function, first manifest under stress and later seen under resting conditions. It is striking that the young dKO mice (5 to 6 weeks old) at rest exhibit systolic dysfunction (hemodynamic and EF abnormalities). This and an abnormally high heart-to-body weight ratio indicate severe cardiac dysfunction. Furthermore, in humans with heart disease and SR-BI/apoE dKO mice, anesthesia can induce substantial conductance abnormalities (eg, brady-arrhythmias and AV blocks). Thus, these dKO mice are a useful model to investigate the mechanisms underlying the development of complex CAD and MI. They should also be useful for preclinical testing of potential genetic and/or pharmacological therapies for CHD.

EXAMPLE 3

Analysis of the Abnormal Lipoproteins in SR-BI/Apo E Double Knockout Mice.

To study the effects of a lack of expression of the gene encoding the Scavenger Receptor, class B type I (SR-BI) on atherosclerosis, mice deficient in SR-BI (SR-BI KO mice) were crossed to mice deficient in apolipoprotein E (apo E KO mice), as described in Example 2. Mice deficient in both SR-BI and apo E (SR-BI/apo E double KO mice) did not survive beyond 8-9 weeks of age. Analysis of atherosclerosis in these mice revealed extensive atherosclerotic plaque in the aortic sinuses of SR-BI/apo E double KO mice at 5-7 weeks of age, at which time, no atherosclerotic plaque formation was detectable in mice deficient in either SR-BI or apo E alone. Further analysis of SR-BI/apo E double KO mice revealed that the animals died as the result of progressive heart block (major cardiac conduction defects), as revealed by changes in electrocardiograms and extensive cardiac fibrosis. These were accompanied by coronary artery atherosclerosis. Complete occlusion of coronary arteries with a lipid-poor material which appears to represent the formation of occlusive fibrin/platelet clots, strongly suggests that the mice die of myocardial infarctions due to atherosclerosis/thrombosis, just like humans.

The HDL receptor SR-BI mediates the selective uptake of plasma HDL cholesterol by the liver and steroidogenic tissues. As a consequence, SR-BI can influence plasma HDL cholesterol levels, HDL structure, biliary cholesterol concentrations, and the uptake, storage and utilization of cholesterol by steroid hormone producing cells. Homozygous null SR-BI knockout mice show that SR-BI is required for maintaining normal biliary cholesterol levels, oocyte development and female fertility. SR-BI/apoE double homozygous knockout mice also show that SR-BI can protect against early onset atherosclerosis. Although the mechanisms underlying the effects of SR-BI loss on reproduction and atherosclerosis have not been established, potential causes include changes in: i) plasma lipoprotein levels and/or structure, ii) cholesterol flux into or out of peripheral tissues (ovary, aortic wall), and iii) reverse cholesterol transport, as indicated by the significant reduction of gallbladder bile cholesterol levels in SR-BI and SR-BI/apoE double knockout mice relative to controls. Crosses between apoE KO mice, which on a chow diet spontaneously develop atherosclerosis at around 3 months of age, and SR-BI KO mice clearly show that genetically suppressing SR-BI activity in apoE KO mice dramatically accelerates the onset of atherosclerosis.

Materials and Methods

Animals

Mice (mixed C57BL/6×129 background) were housed and fed a normal chow diet. SR-BI$^{-/-}$ mice and apoE$^{-/-}$ mice (The Jackson Laboratory were mated and the double heterozygous offspring were intercrossed. The resulting SR-BI$^{+/-}$ ApoE$^{-/-}$ offspring were mated to produce single apoE KO and double SR-BI/apoE KO animals. Genotypes were determined by PCR analysis (see The Jackson Laboratory web site). Estrus cycles were followed by vaginal cytology and external appearance. Superovulation was induced by intraperitoneal injection of 5 IU each of pregnant mare's serum (Calbiochem) and human chorionic gonadotropin (Organon). Pseudopregnancy was induced by mating (confirmed by detection of vaginal seminal plug) with vasectomized males (Taconic). Ovaries were harvested and prepared for sectioning as described below, and oocytes and preimplantation embryos were harvested and cultured in KSOM medium with amino acids (Specialty Media).

Plasma and Bile Analysis

Blood was collected in a heparinized syringe by cardiac puncture from mice fasted overnight. Plasma was subjected to FPLC analysis, either immediately after isolation or after storage at 4° C. Total cholesterol was assayed. Cholesterol from non-apoB containing lipoproteins was determined either using the EZ HDL kit (Sigma, based on an antibody which blocks detection of cholesterol in non-HDL lipoproteins, and validated by us using human or mouse lipoproteins, not shown) or after precipitation with magnesium/dextran sulfate (Sigma). Plasma (0.4 µl) and FPLC fractions or pools were analyzed by SDS-polyacrylamide or agarose gel electrophoresis and immunoblotting with chemiluminescence detection using primary anti-apolipoprotein antibodies (Sigma, or gifts from J. Herz and H. Hobbs) and corresponding horseradish peroxidase coupled secondary antibodies (Jackson Immuno Research or Amersham). The Attophos chemifluorescence kit (Amersham) and an alkaline phosphatase coupled goat anti-rabbit secondary antibody (gift from D. Housman) were used with a Storm Fluorimager (Molecular Dynamics) for quantitative analysis. Plasma progesterone concentrations were determined by radioimmunoassay (Diagnostics Products Corp, Los Angeles, Calif.). Cholesterol was extracted from gallbladder bile and assayed. Histology and immunofluorescence microscopy: Mice anesthetized with 2.5% avertin were perfused through the left ventricle with 20 ml of ice cold PBS containing 5 mM EDTA. Hearts were collected directly, or the mice were perfused (5 ml) with paraformaldehyde and the hearts collected and treated. Hearts and ovaries were frozen in Tissue Tek OCT (Sakura, Torrance, Calif.). Serial cross sections (10 µm thickness through aortic sinuses, 5 µm for ovaries, Reichert-Jung cryostat) were stained with oil red O and Meyer's hematoxylin. Images were captured for morphometric analysis using a computer assisted microscopy imaging system and lesion size was quantified as the sum of the cross-sectional areas of each oil red O staining atherosclerotic plaque in a section using NIH Image software. Immunohistochemistry with a monoclonal anti-α smooth muscle actin antibody (Sigma, gift from R. Hynes) was performed). Cumulus/oocyte complexes, isolated from the oviducts of superovulated females or denuded oocytes (zona pellucida removed) were immunostained with polyclonal rabbit anti-murine SR-BI antibodies gift from K. Kozarsky) and Cy3-labeled donkey anti-rabbit secondary antibodies (gift from R. Rosenberg).

Statistical Analysis

Data were analyzed using either a two-tailed, unpaired Student t-test (total or EZ HDL cholesterol from plasma, bile or FPLC fractions, progesterone and apoA-I levels) or an unpaired nonparametric Kruskall-Wallis test (atherosclerotic plaque lesion sizes) (Statview and Microsoft Excel). Values are presented as means ± standard deviations.

Results and Discussion

To analyze the effects of SR-BI on atherosclerosis, SR-BI KO and apoE KO (spontaneously atherosclerotic) mice were crossed and the lipoprotein profiles and development of atherosclerosis in the single and double homozygous KO females at 4-7 weeks of age compared. Results for males were similar, except as noted. As reported in example 1, plasma total cholesterol in the single SR-BI KOs was increased relative to controls, because of an increase in large, apoE-enriched HDL particles, while the even greater relative plasma cholesterol increase in the single apoE KOs was a consequence of a dramatic increase in cholesterol in VLDL and IDL/LDL size particles. There was increased plasma cholesterol in the double KOs relative to the single apoE KOs, mainly in VLDL size particles. This might have occurred if SR-BI, which can bind apoB containing lipoproteins, directly or indirectly contributes to the clearance of the cholesterol in VLDL size particles in single apoE KO mice (reduced clearance in its absence).

The normal size HDL cholesterol peak seen in the single apoE KOs virtually disappeared in the double KOs. However, no statistically significant differences (P=1.0) in plasma levels of HDL's major apolipoprotein, apoA-I, were detected. Based on the analysis of lipoproteins in the single SR-BI KO mice, abnormally large HDL-like particles were expected to appear in the double KOs. Indeed, the loss of normal sized HDL cholesterol and apoA-I in the double KOs was accompanied by a shift of the apoA-I into the VLDL and IDL/LDL size fractions. Furthermore, analysis of HDL-like cholesterol in the FPLC fractions using the EZ HDL assay provides evidence for the presence of abnormally large HDL-like particles in the double KO mice. In the single apoE KO males, most of this cholesterol was in particles with the size of normal HDL, while in their double KO counterparts almost all of this cholesterol was in abnormally large particles. In addition, there was approximately 3.7-fold more of this HDL-like cholesterol in the double (133±24 mg/dl) than in the single (36±16 mg/dl, P=0.005) KO mice. These increases in the amounts and sizes of HDL-like cholesterol by inactivation of the SR-BI gene in an apoE KO background were reminiscent of those seen in a wild-type background (approximately 2.2-fold increase in cholesterol, although the HDL-like particles in the double KO mice were much larger and more heterogeneous than those in the SR-BI single KO mice. A similar trend was seen for female mice, except that there were increased levels of abnormally large HDL-like cholesterol in the single apoE KO females relative to males. Preliminary cholesterol measurements using magnesium/dextran sulfate precipitation of lipoproteins support the EZ HDL findings of large HDL in the double KO animals.

Additional evidence for abnormally large HDL-like particles in the IDL/LDL size range from both males and females was obtained using agarose gel electrophoresis and immunoblotting. There was a significant reduction in the amount of immunodetectable apoB present in the IDL/LDL-sized particles from the double KOs relative to the single apoE KOs, even though there was as much or more total cholesterol in these fractions in the double KOs. In addition, there was significantly greater heterogeneity in the electrophoretic mobilities of apoA-I containing IDL/LDL-sized particles. This was in part due to the presence of novel apoA-I containing, apoB-free, HDL-like particles. In contrast, most of the apoA-I in the single apoE KOs appeared to comigrate with apoB. Thus, it appears that normal size HDL in the single apoE KO animals was replaced by very large (VLDL/IDL/LDL-size) HDL-like particles in the double KO animals. It is possible that normal size HDL is converted into these large HDL-like particles in the absence of both apoE and SR-BI because of substantially reduced selective (SR-BI mediated) and apoE-mediated uptake or transfer of cholesterol from HDL particles.

In addition to examining plasma cholesterol, biliary cholesterol was measured in the mice. Cholesterol levels in gallbladder bile were significantly reduced in SR-BI single KO (30%, P<0.005) and SR-BI/apoE double KO (47%, P<0.0005) mice relative to their SR-BI$^{+/+}$ controls. This is consistent with the previous finding that hepatic overexpression of SR-BI increases biliary cholesterol levels and indicates that SR-BI may normally play an important role in the last stage of reverse cholesterol transport—transfer of plasma HDL cholesterol into bile. The data also suggest that apoE expression can regulate biliary cholesterol content in a SR-BI KO, but not SR-BI$^{+/+}$, background.

Atherosclerosis in the animals was assessed by analyzing plaque areas in aortic sinuses and the effects of SR-BI gene disruption on plasma lipoproteins in apoE KO mice. Mice were 4-7 weeks old. Plasma apoA-I levels (right, mean±SD, expressed as relative units) were determined by SDS-polyacrylamide (15%) gel electrophoresis followed by quantitative immunoblotting for apoE$^{-/-}$ (n=7) and SR-BI$^{-/-}$ apoE$^{-/-}$ females (n=5) (P=0.1). Lipoprotein cholesterol profiles: Plasma lipoproteins from individual apoE$^{-/-}$ or SR-BI$^{-/-}$ apoE$^{-/-}$ females were separated based on size (Superose 6-FPLC) and total cholesterol in each fraction (expressed as mg/dl of plasma) was measured. Pooled Superose 6-FPLC fractions (approximately 21 μl per pool) from females in an independent experiment were analyzed by SDS-polyacrylamide gradient (3-15%) gel electrophoresis and immunoblotting with an anti-apoA-I antibody (18). Each pool contained 3 fractions and lanes are labeled with the number of the middle fraction in each pool. Average EZ HDL cholesterol FPLC profiles for apoE$^{-/-}$ or SR-BI$^{-/-}$ apoE$^{-/-}$ males (n=3) or females (n=3). Agarose gel electrophoresis and immunoblotting: Pooled fractions (11-21, 3.5 μl) from the IDL/LDL region of the lipoprotein profile from individual apoE$^{-/-}$ or SR-BI$^{-/-}$ apoE$^{-/-}$ females were analyzed using either anti-apoA-I or anti-apoB antibodies. Migration was upward from negative to positive. Gallbladder biliary cholesterol (mean±SD): Total gallbladder biliary cholesterol from both male and female mice of the indicated genotypes (n=10 or 11 per genotype) was measured. Except for the wild-type and apoE$^{-/-}$ values, all pairwise differences were statistically significant (P<0.025-0.0005).

To determine the effects of SR-BI gene disruption on atherosclerosis in apoE KO mice, atherosclerosis in SR-BI$^{-/-}$ (n=8, 4-6 weeks old), apoE$^{-/-}$ (n=8, 5-7 weeks old), or SR-BI$^{-/-}$ apoE$^{-/-}$ (n=7, 5-6 weeks old) female mice was analyzed in cryosections of aortic sinuses stained with oil red O and Meyer's hematoxylin as described in Methods. Representative sections through the aortic root region and cross-sectional areas of oil red O stained lesions in the aortic root region, showed average lesion areas (mm$^2$±SD) for SR-BI$^{-/-}$ apoE$^{-/-}$, apoE$^{-/-}$ or SR-BI$^{-/-}$ mice, respectively, were as follows 0.10±0.07, 0.002±0.002, and 0.001±0.002 (P=0.0005). Also see Table II quantitative analysis of females; qualitative analysis of a smaller sample of males gave similar results. There were virtually no detectable lesions in the single KO animals at this relatively young age (4-7 weeks). However, there was substantial, statistically significant, lesion development in the double KOs in the aortic root region, elsewhere in the aortic sinus (Table II), mately 600 mg/dl). It is theought the similarities arise in part because the very high levels of large lipoproteins in the fat-fed single apoE KO might block the ability of SR-BI to interact with HDL and other ligands (functional SR-BI deficiency due to competition), or because of dietary suppression of hepatic SR-BI expression.

TABLE II

Average lesion sizes in the aortic sinuses of mice deficient in SR-BI, apoE, or both.

| | Mean lesion size (mm$^2$)* | | | | |
|---|---|---|---|---|---|
| Genotype | Aortic Root | Partial Valve Cusps | Valve Attachment Sites | Proximal Aorta | Overall Mean‡ |
| SR-BI$^{-/-}$ | 0.001 ± 0.002(8) | 0.0003 ± 0.0008(8) | 0 ± 0(8) | 0 ± 0(6) | 0.0004 ± 0.001(6) |
| apoE$^{-/-}$ | 0.002 ± 0.002(9) | 0.0006 ± 0.0009(9) | 0.001 ± 0.002(9) | 0.0002 ± 0.0003(9) | 0.001 ± 0.002(9) |
| SR-BI$^{-/-}$ apoE$^{-/-}$ | 0.10 ± 0.07(7) | 0.07 ± 0.07(7) | 0.02 ± 0.01(6) | 0.02 ± 0.02(6) | 0.04 ± 0.04(6) |
| P value† | 0.0005 | 0.006 | 0.002 | 0.003 | 0.001 |

*Values are the means ± SD (number of animals indicated in parentheses).
‡Means of combined values from the regions of the aortic root partial valve cusps, valve attachment sites and proximal aorta.
†Lesion sizes in each region were compared using the Kruskall-Wallis test and in coronary arteries. The lipid-rich lesions were cellular (hematoxylin stained nuclei were seen at high magnification) and in some cases had a cellular cap which stained with antibodies to smooth muscle actin. Thus, the atherosclerotic plaques were relatively advanced.

Potential causes of the dramatically accelerated atherosclerosis in the double KOs include: i) changes in relative amounts of cholesterol in proatherogenic (e.g., increased VLDL sized or abnormally large HDL-like particles) and antiatherogenic (e.g., loss of normal HDL) lipoproteins, ii) altered flux of cholesterol into or out of the aortic wall, perhaps directly due to SR-BI-mediated efflux (17, 38, 39), iii) decreases in RCT, suggested by the generation of abnormally large, HDL-like particles and decreased biliary cholesterol levels due to absence of hepatic SR-BI activity, and iv) changes in other metabolic/organ systems which might influence the cardiovascular system. For example, there was significant accumulation of oil red O staining lipids in other tissues, including the myocardium, in the double, but not single, KO animals. In addition, at 5-6 weeks of age when the double KOs were studied, they were somewhat smaller (approximately 20% lower weight) than single apoE KO controls.

While most did not exhibit overt signs of illness at that time, they all died suddenly around 8-9 weeks of age. Electrocardiographic studies indicated that premature death of the double KOs was due to progressive heart block (cardiac conduction defects) and histology revealed extensive cardiac fibrosis and narrowing or occlusion of the coronary arteries, suggesting myocardial infarction (MI) due to advanced atherosclerotic disease.

The anti-atherosclerotic effect of SR-BI expression in apoE KO mice is consistent with the reports that adenovirus- or transgene-mediated hepatic overexpression of SR-BI in the cholesterol and fat-fed LDLR KO mouse reduces atherosclerosis. Thus, pharmacologic stimulation of endogenous SR-BI activity may be antiatherogenic, possibly because of its importance for RCT. The accelerated atherogenesis and loss of normal size HDL cholesterol in the double KOs resembles that reported for high-fat diet fed single apoE KO mice; although those mice have far higher total plasma cholesterol levels (1800-4000 vs. approxi-

EXAMPLE 4

Prevention or Treatment of Atherosclerosis in SR-BI Knockout Mice

The animals described in the proceeding examples are useful to screen for compounds that are effective for the prevention or treatment of atherosclerosis and heart disease. Several studies were conducted to demonstrate this.

Materials and Methods

Animals

Mice were housed and fed a normal chow diet or chow (Teklad 7001) supplemented with 0.5% (wt/wt) 4,4'-(isopropylidene-dithio)-bis-(2,6-di-tertbutylphenol (probucol; Sigma Chemical Co., St. Louis, Mo., USA). Mouse strains (genetic backgrounds) were: wild-type and SR-BI KO (both 1:1 mixed C57BL/6×129 backgrounds), apoA-I KO (C57BL/6; The Jackson Laboratory, Bar Harbor, Me., USA). Double SR-BI/apoA-I KO mice were produced by (a) mating SR-BI KO males with apoA-I KO females, (b) transferring the resulting embryos into Swiss Webster recipients, and (c) intercrossing the double heterozygous offspring. Colonies were maintained by crossing double-KO males with females heterozygous for the SR-BI null mutation and homozygous for the apoA-I mutation to optimize the low yield of SR-BI homozygotes.

Results

Effects of Genetic Disruption of the apoA-I Gene or Probucol Treatment on the Fertility of Female SR-BI KO Mice Wild-type males were mated with female SR-BI KO (n=13, average litter size=1, 2- to 6-month mating), SR-BI/apoA-I KO (n=17, dark gray bars, average litter size=2.2, 4-month mating), probucol-fed SR-BI KO (n=14s, average litter size=5.7, 1- to 2-month mating), and probucol-fed wild-type (n=9, white bars, average litter size=5.3, 1- to 2-month mating) mice.

In the first study, PROBUCOL was fed to a mating pair (Apo E−/− and SR-BI+/−). The offspring, who have had PROBUCOL since conception, were weaned at three weeks of age. They continued to receive PROBUCOL in the chow. At 6 weeks, when typically 50% of the animals are dead in the absence of treatment, there is no abnormal phenotype, as measured by MRI of heart function, ECG, echocardiogram, and histology. There is no evidence of atherosclerosis.

At 7-8 months, most of the animals receiving PROBUCOL are still alive. However, they do have substantial atherosclerosis and some myocardial infarctions. In contrast, normal wild-type mice show no evidence of heart disease or atherosclerosis.

In a second study, animals receiving PROBUCOL were taken off of the treatment at six weeks of age. All of the animals die within 10-12 weeks.

In a third study, the animals were not treated with PROBUCOL until either weaning (three weeks of age) or approximately 4½ weeks of age (average age of death is six weeks of age). They were then fed PROBUCOL. One-half of the animals not receiving PROBUCOL until 4½ weeks of age die within a few weeks. The majority of those fed PROBUCOL at weaning survive a few months.

These results demonstrate that drugs can be used as preventatives as well as therapeutics.

Modifications and variations of the methods and materials described herein will be obvious to those skilled in the art and are intended to be encompassed by the following claims. The teachings of the references cited herein are specifically incorporated herein.

We claim:

1. A method for identifying compounds for treating or preventing atherosclerosis or cardiovascular disease comprising
   administering compounds that may have an effect on disorders selected from the group consisting of cardiac fibrosis, myocardial infarction, defects in electrical conductance, atherosclerosis, unstable plaque, and stroke to a mouse having decreased expression of active SR-BI and Apo-E wherein the mouse develops atherosclerotic plaque in the aortic sinuses and progressive heart block and
   determining the effect of the compound on cardiac fibrosis, myocardial infarction, defects in electrical conductance, atherosclerosis, unstable plaque, stroke, diseases associated with abnormal cardiac structure or function or elevated cholesterol or lipoprotein levels in the mouse relative to control mice not treated with compound.

2. The method of claim 1 wherein the mouse is a homozygous knockout for apolipoprotein.

3. The method of claim 1 wherein the compound is an antioxidant.

4. The method of claim 1 wherein the compound is hypocholesterolemic.

5. The method of claim 1 wherein the compounds is both an antioxidant and hypocholesterolemic.

6. The method of claim 1 wherein the compound is 4,4'-(isopropylidenedithio) bis(2,6-di-tert-butylphenol), monoesters and other derivatives thereof.

7. The method of claim 1 wherein the compound is 2,3-Dihydro-5-hydroxy-2,2-dipentyl-4,6-di-tert-butyl-benzofuran or a derivative thereof.

8. The method of claim 1 wherein the compounds are selected from the group consisting of vitamin E and vitamin C.

9. The method of claim 1 wherein the mouse is a heterozygous or homozygous SR-BI and Apo E knockout.

10. The method of claim 1 wherein the mouse is treated with a compound which lowers the level of SR-BI.

* * * * *

UNITED STATES PATENT AND TRADEMARK OFFICE
CERTIFICATE OF CORRECTION

PATENT NO. : 7,361,684 B2  
APPLICATION NO. : 10/147651  
DATED : April 22, 2008  
INVENTOR(S) : Monty Krieger, Anne Braun and Helena E. Miettinen It is certified that error appears in the above-identified patent and that said Letters Patent is hereby corrected as shown below:

Column 1, lines 13-18, replace "The U.S. government has certain rights to this invention by virtue of Grants HL41484, HI-52212, and HL20948 from the National Institutes of Health-National Heart, Lung and Blood Institute to Monty Kreiger and HL63609 and HL53793 to M. Simons and M.J.P. from the US National Institutes of Health" with --This invention was made with Government support under Grant Nos. P01 HL041484 and R01 HL052212, awarded by the National Institutes of Health. The Government has certain rights in this invention--.

Signed and Sealed this  
Fourth Day of October, 2011

David J. Kappos  
*Director of the United States Patent and Trademark Office*

UNITED STATES PATENT AND TRADEMARK OFFICE
CERTIFICATE OF CORRECTION

PATENT NO. : 7,361,684 B2  Page 1 of 1
APPLICATION NO. : 10/147651
DATED : April 22, 2008
INVENTOR(S) : Monty Krieger, Anne Braun and Helena E. Miettinen It is certified that error appears in the above-identified patent and that said Letters Patent is hereby corrected as shown below:

Column 1, lines 13-18, replace "The U.S. government has certain rights to this invention by virtue of Grants HL41484, HI-52212, and HL20948 from the National Institutes of Health-National Heart, Lung and Blood Institute to Monty Kreiger and HL63609 and HL53793 to M. Simons and M.J.P. from the US National Institutes of Health" with --This invention was made with government support under Grant Nos. R01 HL052212 and F01 HL041484 awarded by the National Institutes of Health. The government has certain rights in the invention--.

This certificate supersedes the Certificate of Correction issued October 4, 2011.

Signed and Sealed this
Twenty-first Day of February, 2012

David J. Kappos
*Director of the United States Patent and Trademark Office*

SEQUENCE LISTING

<160> NUMBER OF SEQ ID NOS: 3

<210> SEQ ID NO 1
<211> LENGTH: 26
<212> TYPE: DNA
<213> ORGANISM: Artificial Sequence
<220> FEATURE:
<223> OTHER INFORMATION: Synthetic oligonucleotide PCR primer

<400> SEQUENCE: 1
tgaaggtggt cttcaagagc agtcct                                    26

<210> SEQ ID NO 2
<211> LENGTH: 26
<212> TYPE: DNA
<213> ORGANISM: Artificial sequence
<220> FEATURE:
<223> OTHER INFORMATION: Synthetic oligonucleotide PCR primer

<400> SEQUENCE: 2
gattgggaag acaatagcag gcatgc                                    26

<210> SEQ ID NO 3
<211> LENGTH: 25
<212> TYPE: DNA
<213> ORGANISM: Artificial sequence
<220> FEATURE:
<223> OTHER INFORMATION: Synthetic oligonucleotide PCR primer

<400> SEQUENCE: 3
tatcctcggc agacctgagt cgtgt                                     25